United States Patent [19]

Archibald et al.

[11] Patent Number: 4,778,802
[45] Date of Patent: Oct. 18, 1988

[54] HETEROCYCLIC COMPOUNDS

[75] Inventors: John L. Archibald, Farnham Royal; Terence J. Ward, Maidenhead, both of England

[73] Assignee: John Wyeth & Brother, Ltd., Maidenhead, England

[21] Appl. No.: 930,596

[22] Filed: Nov. 12, 1986

[30] Foreign Application Priority Data

Nov. 15, 1985 [GB] United Kingdom ............ 8528234

[51] Int. Cl.$^4$ .................. C07D 215/02; A61K 403/06
[52] U.S. Cl. .................................... 514/314; 546/171; 546/176; 546/177
[58] Field of Search ............... 546/176, 177; 514/314

[56] References Cited

U.S. PATENT DOCUMENTS

| | | | |
|---|---|---|---|
| 2,456,911 | 12/1948 | Bruce | 546/171 |
| 4,073,790 | 2/1978 | Archibald et al. | 260/293.73 |
| 4,177,279 | 12/1979 | Archibald et al. | 424/267 |
| 4,199,590 | 4/1980 | Ward | 424/267 |
| 4,209,521 | 6/1980 | Archibald et al. | 424/267 |
| 4,426,387 | 1/1984 | Archibald et al. | 424/267 |
| 4,472,403 | 9/1984 | Trijzelaar et al. | 546/177 |
| 4,563,466 | 1/1986 | Archibald et al. | 514/319 |

FOREIGN PATENT DOCUMENTS 0007525 7/1979 European Pat. Off. .
2034305 6/1980 United Kingdom .
2106109 4/1983 United Kingdom .

Primary Examiner—Richard L. Raymond
Assistant Examiner—D. B. Springer
Attorney, Agent, or Firm—Arthur G. Seifert

[57] ABSTRACT

The invention relates to compounds of formula

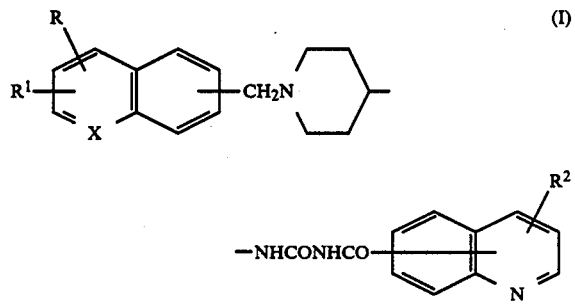

or a salt thereof, wherein =X— is =CH— or =N—, R and $R^1$ independently represent hydrogen, halogen or lower alkoxy and $R^2$ is hydrogen or a substituent selected from halogen, lower alkyl, lower alkoxy or halo-lower alkyl which compounds exhibit psychotropic activity and are useful as antidepressants.

10 Claims, No Drawings

HETEROCYCLIC COMPOUNDS

This invention relates to heterocyclic compounds, more particularly piperidine derivatives, to processes for preparing them and to pharmaceutical compositions containing them.

in our UK Patent Publication No. 2073176B there are described and claimed a class of piperidine derivatives which exhibit psychotropic activity in standard pharmacological test procedures and are potentially useful as anti-depressants. In general the compounds are specific inhibitors of 5-hydroxytryptamine re-uptake in vitro and in vivo, and therefore are also useful in any other therapeutic applications where such pharmacological specificity is beneficial. The piperidine derivatives of UK Patent Publication No. 2073176B have the formula (II)

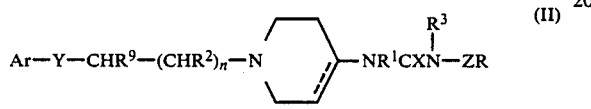

and acid addition and quaternary ammonium salts thereof, wherein the dotted line represents an optional bond, Ar represents a ring system of formula

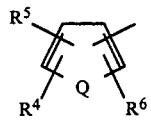

in which Q is O, S, $-CR^7=CR^8-$, $-N=CR^8-$ and $-N=N-$; $R^4$, $R^5$ and $R^6$, and $R^7$ and $R^8$ when present, each represent hydrogen or a substituent selected from halogen, lower alkyl, lower alkenyl, lower alkoxy, $NO_2$, $NH_2$, haloloweralkyl, hydroxyloweralkyl, aminoloweralkyl, substituted amino, loweralkoxycarbonyl, cyano, $CONH_2$ and hydroxy; and additionally either $R^4$ and $R^5$ when adjacent or $R^6$ and $R^8$ when adjacent, together with the carbon atoms to which they are attached also represent a fused five or six membered carbocyclic or heterocyclic ring optionally carrying one or more substituents as defined above; R is an optionally substituted aryl or heteroaryl radical or a cycloalkyl radical containing 5 to 7 carbon atoms; $R^1$, $R^2$, $R^3$ and $R^9$ are each hydrogen or a lower alkyl group; n is 0 or 1; X is $=O$ or $=S$; Y is $-O-$ or a direct bond and Z is $-CO-$ or $-CH_2-$ with the provisos that (i) when Ar is unsubstituted phenyl and $R^9$ is hydrogen then Y is $-O-$ and (ii) when Z is $CH_2$ and Ar represents phenyl or pyridyl group either of which may be substituted then $R^1$ is hydrogen.

The term 'lower' as used in connected with alkyl or alkoxy groups means that such groups contain 1 to 6 carbon atoms. 'Substituted amino' includes groups such as alkyl- ior dialkyl-amino, acylamino e.g. lower alkylcarbonylamino, ureido or sulphonylamino, e.g. lower alkylsulphonamido or di-lower-alkylsulphonylamino.

Pharmaceutical compositions comprising compounds of formula (II) are claimed in our UK Patent Publication No. 2108489B.

The compounds of formula II were tested for psychotropic activity by their ability to inhibit p-chloroamphetamine (pCA) induced hyperactivity and/or by their ability to inhibit 5-hydroxytryptamine (5-HT) re-uptake in brain slices.

We have now surprisingly found that a small class of compounds, not specifically disclosed in either of the above mentioned specifications, having formula II above wherein Ar is naphthyl or quinolyl and R is quinolyl are extremely potent inhibitors of pCA induced syndrome.

Accordingly this invention provides compounds of formula

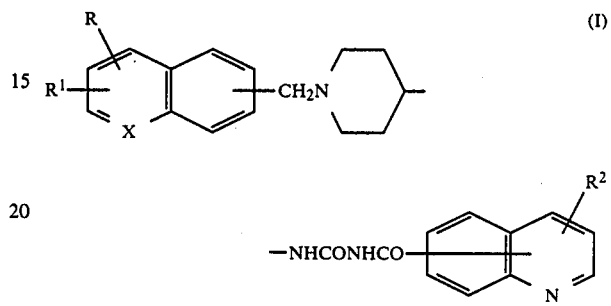

wherein $=X$ is $=CH$ or $=N-$, R and $R^1$ independently represent hydrogen, halogen or lower alkoxy and $R^2$ is hydrogen or a substituent selected from halogen, lower alkyl, lower alkoxy or halolower alkyl. "Lower" for lower alkyl and lower alkoxy means having 1 to 6 atoms, with 1 to 3 carbon atoms being preferred. Halogen refers to fluorine, chlorine and bromine of which fluorine and chlorine are preferred. "Halolower alkyl" refers to a group having 1 to 6 carbon atoms and 1 to 6 halogen atoms, preferably the same halogen atom. Fluorine and chlorine are the preferred halogen atoms for a halolower alkyl group. Preferred examples of halolower alkyl are trifluoromethyl, trichloromethyl, trichloroethyl, trifluoroethyl, tetrachloroethyl, tetrafluoroethyl, pentachloroethyl, and pentafluoroethyl. Preferred examples of the group R and $R^1$ of Formula I are hydrogen, fluorine, chlorine and methoxy, of which hydrogen and fluorine are most preferred. Also, most preferred, one of R and $R^1$ is hydrogen and the other is fluorine, chlorine, or methoxy, of which fluorine is most preferred; or both R and $R^1$ are hydrogen.

Especially preferred compounds of formula I have a napth-2-ylmethyl or quinol-6 or 7-ylmethyl group bonded to the piperidine moiety, each optionally substituted as described above. Most preferably the compounds have a 6-fluoronaphth-2-ylmethyl or unsubstituted quinol-6-ylmethyl group.

Also preferred are compounds wherein the urea function is substituted by a quinol-6- or 7-oyl group optionally substituted as herein before described. Most preferably the urea function is substituted by an unsubstituted quinol-6-oyl group.

Preferred compounds of the invention are N-[[[1-(2-naphthalenylmethyl)-4-piperidinyl]amino]-carbonyl]-6-quinolinecarboxamide, (A)

N-[[[1-(quinol-6-ylmethyl)-4-piperidinyl]amino]-carbonyl]-6-quinolinecarboxamide, (B) and N-[[[1-(6-fluoro-2-naphthalenylmethyl)-4-piperidinyl]-amino]-carbonyl]-6-quinolinecarboxamide. (C)

Representative compounds of this invention were tested for their ability to inhibit pCA induced syndrome in rats by the standard procedure described below:

Inhibition of p-chloroamphetamine (pCA)-induced stereotypy

Vehicle or drug (5 dose levels) were administered p.o. to six groups of 6-8 male Sprague-Dawley rats (300-400 g) followed, 90 minutes later, by pCA (10 mg/kg i.p.). The animals were then placed in individual observation chambers and, 30 minutes after pCA administration, the intensity of the pCA-induced 5-HT syndrome was assessed according to the following scoring system:

| hind-limb abduction<br>head-weaving<br>fore-paw treading | } | 0, 1, 2 or 3 according to severity |
|---|---|---|
| tremor | | 0 (absent) or 1 (present) |

Therefore, the maximum score for each animal was 10.

The inhibition of pCA induced stereotypy is calculated for each dose level as follows:

$$\frac{C - T}{C} 100\%$$

where

C=control group total score at 30 minutes post pCA.

T=group total score of treated group at 30 minutes post pCA.

For each dose a % effect is calculated.

The results obtained from the tests using 5 different dose levels of the drug allow the $ED_{50}$ value (i.e. the dose required to produce 50% inhibition of pCA induced stereotypy) to be calculated.

In the aforementioned test the representative compounds A, B and C antagonised pCA-induced stereotypy in a dose-dependent manner and gave the following $ED_{50}$ values:

| Compounds of Formula I | $ED_{50}$ (mg/kg) |
|---|---|
| A | 2.7 |
| B | 6.5 |
| C | 2.1 |

The test was carried out using the free bases except for compound C which was tested in the form if its maleate salt and the result corrected for amount of active material.

These values are markedly more potent than values found for compounds disclosed in the specification of UK Patent Publication No. 2073176B. At 50 mg/kg the compounds A, B and C showed a 99% inhibition of syndrome.

In the same test one of the most preferred compounds from UK Patent Publication No. 2073176B namely, 1-benzoyl-3-[1-(naphth-2-ylmethyl)piperid-4-yl]urea (panuramine) had an $ED_{50}$ of 16.2 mg/kg (monohydrochloride corrected for amount of active ingredient). At 50 mg/kg this compound showed a ca. 78% inhibition of syndrome.

In addition compounds of the present invention have allso been found to possess a long duration of action in reducing the intensity of the pCA syndrome. In a test involving administering compound C at a dose level of 6 mg/kg p.o. to a group of 8 male Sprague-Dawley rats the percentage inhibition of pCA-induced stereotypy (assessed according to the method above) at various times after administration of 5-HT inhibitor was as shown below:

| Time from 5-HT dosing | % Inhibition of pCA induced stereotypy |
|---|---|
| 2 | ca. 79% |
| 6 | 82.8 |
| 12 | 56.9 |
| 16 | 57.6 |

In a related test (with modified scoring) panuramine at a dose level of 15 mg/kg produced a 65.1% inhibition after two hours and 12.2% inhibition after 16 hours indicating a much shorter duration of action. A long duration of action has the advantage that dosing is less frequent and accordingly patient compliance with the dosing regimen is generally improved, especially if reduced to once a day.

The compounds B and C were also tested for their ability to potentiate 5-hydroxy-L-tryptophan induced behavioural syndrome in rats. The test procedure is described below (updated from that described in UK No. 2073179B).

Potentiation of 5-hydroxytryptophan (5-HTP)-induced behaviour

Groups of 10 male Sprague-Dawley rats (310-360 g) were dosed p.o. with vehicle or drugs. Ninety minutes later 5-HTP (50 mg/kg s.c.) was administered and the animals placed in individual observation chambers (peripheral decarboxylation was prevented by 25 mg/kg i.p. carbidopa administered 60 minutes before 5-HTP). Head shakes were counted over the period 30-45 minutes after 5-HTP and the intensity of the 5-HT syndrome was scored immediately afterwards using the system described for the pCA procedure above. Percentage potentiation of syndrome was calculated as follows:

| hind-limb abduction<br>head-weaving | 0, 1, 2 or 3 according to severity |
|---|---|
| tremor<br>fore-paw treading | 0 (absent) or 1 (present) |

Percentage potentiation was calculated from the following:

$$\frac{\text{test score} - \text{control score}}{\text{maximum possible score} - \text{control score}} \times 100$$

In this test compounds B and C had an $ED_{50}$ value of 7.3 mg/kg and 2.4 mg/kg respectively (the latter corrected for amount of active ingredient).

These values are also markedly lower than the value found for the compound panuramine HCl salt which in the same test had an $ED_{50}$ value of 27.4 mg/kg (corrected for amount of base).

In vitro tests have shown that compounds of formula I also have a marked degree of selectivity in inhibiting uptake of 5-HT into rat brain synaptosomes relative to uptake of $^3H$ noradrenaline. The test procedure involved obtaining synaptosomal preparations from male Sprague Dawley rats according to the method of Grey and Whittaker* as modified by Wood & Wyllie.** Aliquots of the synaptosomal preparation were then incubated with tritated noradrenaline (NA) or 5-HT at a temperature of 37° for 4 minutes. The active synaptosomal accumulation of labelled substrate was measured by filtration and scintillation counting. The effect at a range of concentrations of test compound enabled $IC_{50}$ values and selectivity ratios to be calculated.

*Grey and Whittaker,-J. Anat. 96 79 (1962)
**Wood and Wyllie, J. Neurochemistry, 37, 795 (1981)

The values found for compounds B and C and panuramine are shown below:

| Compound | $IC_{50}$ (μM) | | Selectivity Ratio |
|---|---|---|---|
| | 5-HT uptake | NA | |
| B | 0.043 | 8.9 | 207 |
| C | 0.082 | 37.0 | 450 |
| panuramine | 0.063 | 8.5 | 135 |

The compounds of the present invention can be prepared by any of the appropriate general procedures described in our UK Patent Publication No. 2073176B.

In particular the compounds of the present invention can be prepared by reacting a compound of formula

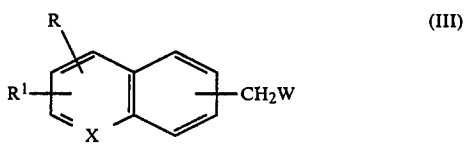
(III)

wherein X, R and $R^1$ are as defined above and W represents a leaving group such as halogen (e.g. chlorine, bromine or iodine), an organic sulphonyloxy radical (e.g. tosyloxy, mesyloxy) or a radical of formula $-OSO_2OR^3$ where $R^3$ is

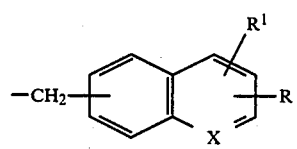

(i.e. sulphate) with a compound of formula IV

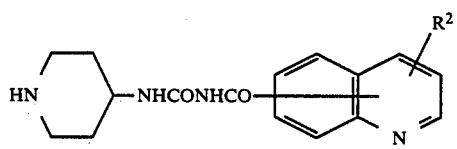
(IV)

wherein $R^2$ is hereinbefore defined.

This reaction is preferably carried out in the presence of base e.g. an alkali metal carbonate such as $K_2CO_3$ or an amine such as triethylamine or diisopropylethylamine, otherwise the reaction may be carried out by heating in the presence of an inert solvent, e.g. toluene.

A second method for preparing the compound of this invention comprises reacting a compound of formula

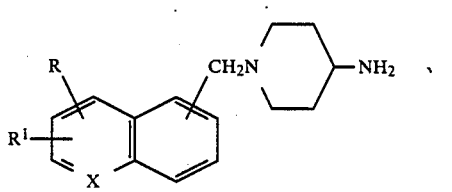
(V)

wherein X, R and $R^1$ are as defined above with a compound of formula

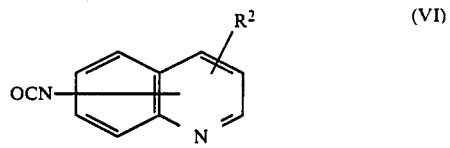
(VI)

wherein $R^2$ is as hereinbefore defined. This reaction is conveniently carried out at room temperature and in an inert solvent. The starting material (V) may be prepared by processes described in UK Patent Specification No. 1,345,872.

A further process for preparing the compounds of this invention comprises reacting the starting material V with a compound of formula

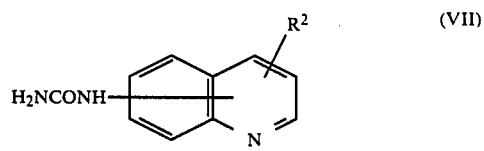
(VII)

wherein $R^2$ is as defined above.

Conveniently this reaction is carried out in the presence of a suitable inert solvent, for example toluene, pyridine, xylene, chlorobenzene, dimethylformamide or dioxan; pyridine being preferred. Preferably the reaction is carried out by heating at reflux until complete.

A still further process for preparing the compound of this invention comprises acylating a compound of formula

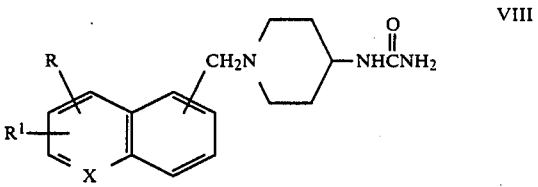
VIII wherein R, $R^1$ and X are as defined above, with an acylating agent containing the group

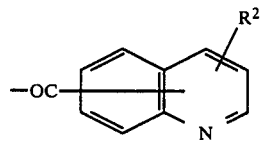

Examples are reactive derivatives of quinoline carboxylic acid such as the acid anhydride, mixed anhydride, acid halide or activated ester such as used in peptide chemistry. Other methods of acylation are well known in the art such as those employing coupling reagents such as carbodiimides, e.g. dicyclohexylcarbodiimide.

The compound of this invention may also be prepared by reducing a compound of formula

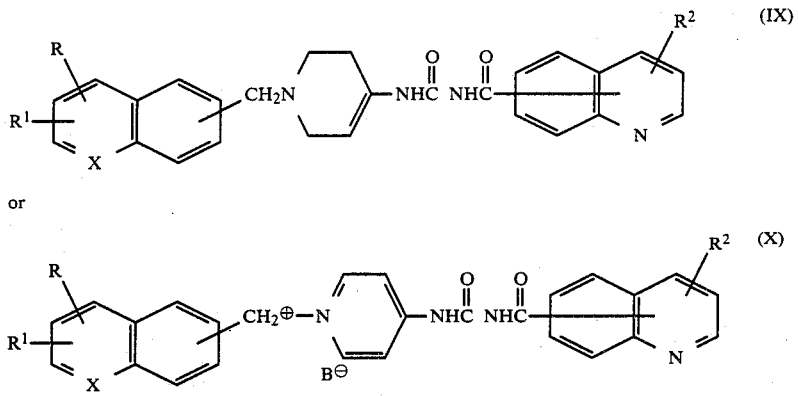

or wherein B represents an anion, e.g. a halide ion. For example catalytic hydrogenation e.g. in the presence of Raney nickel or platinum catalyst gives the compounds of the invention. The reduction may also be effected by a process described and claimed in our UK Patent Specification No. 1542137. Such a reduction process employs an alkali metal borohydride in a secondary alkanol having 3-5 carbon atoms, e.g. isopropanol. Alternatively reduction of the compound of formula (X) using an alkali metal borohydride in methanol gives the dehydropiperidine compound of formula (IX).

Yet a further process for preparing the compound of this invention comprises reacting a compound of formula II wherein W is hydroxy with a compound of formula IV in the presence of a catalyst, e.g. a nickel catalyst such as Raney nickel.

In any of the aforementioned processes the compounds of the invention may be isolated in free base form or as salts, e.g. an acid addition salt. Quaternisation of the tertiary nitrogen of the piperidine ring may be included as an optional after step, e.g. using alkyl or aryl lower alkyl halides, e.g. methyl, iodide, benzyl chloride.

Acid addition salts include salts with pharmaceutically acceptable acids such as the hydrochloric, sulphuric, nitric, hydrobromic, hydroiodic, acetic, citric, tartaric, phosphoric, fumaric, malonic, formic and maleic acid addition salts.

This invention further provides a pharmaceutical composition comprising a compound of formula I or a pharmaceutically acceptable salt thereof in association with a pharmaceutically acceptable carrier. Any suitable carrier known in the art can be used to prepare the pharmaceutical composition. In such a composition, the carrier is generally a solid or liquid or a mixture of a solid and a liquid.

Solid form compositions include powders, granules, tablets, capsules (e.g. hard and soft gelatin capsules), suppositories and pessaries. A solid carrier can be, for example, one or more substances which may also act as flavouring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, perservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilised by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit doses containing appropriate quantities of the active ingredient; the unit dosage forms can be packaged compositions, for example packeted powders, vials, ampoules, prefilled syringes or sachets containing liquids. The unit dosage form can be for example, a capsule or tablet itself, or it can be the appropriate number of any such compositions in package form. The quantity of the active ingredient in a dose of composition may be varied or adjusted from 0.5 mg or less to 750 mg or more, according to the particular need and the activity of the active ingredient. The invention also includes the compounds in the absence of the carrier where the compounds are in unit dosage form.

The following Examples illustrate the invention:

EXAMPLE 1

N-[[[1-(2-Naphthalenylmethyl)-4-piperidinyl]amino]carbonyl]-6-quinolinecarboxamide A suspension of 4-amino-1-(2-naphthalenylmethyl)piperidine (1.4 g, 5.83 mmol) and N-aminocarbonyl-6-quinolinecarboxamide (1.08 g, 5.02 mmol) in pyridine (7 cm$^3$) was refluxed for 7 hours. The mixture was left at room temperature overnight then more 4-amino-1-(2-naphthalenylmethyl)piperidine (0.3 g, 1.4 mmol) was added and refluxing was continued for 5 hours. Undissolved solid was filtered off from the hot mixture and the filtrate was diluted with water (8 cm$^3$) and filtered again. The filtrate was further diluted with water and cooled in ice. The deposited solid was collected and dried (0.46 g,) then recrystallised from ethanol (50 cm$^3$) to give 0.30 g of the title compound, m.p. 211°–13° C.

Analysis Found: C, 73.79; H, 6.07; N, 12.64; $C_{27}H_{26}N_4O_2$ requires C, 73.95; H, 5.98; N, 12.78.

EXAMPLE 2

N-[[[1-(quinol-6-ylmethyl)-4-piperidinyl]amino]carbonyl]-6-quinolinecarboxamide

A suspension of 4-amino-1-(6-quinolinylmethyl)piperdine (1.0 g, 4.15 mmol) and N-aminocarbonyl-6-quinolinecarboxamide (0.7 g, 3.26 mmol) in pyridine (6 ml) was refluxed rapidly for 6 hours. More 4-amino-1-(6-quinolinylmethyl)piperidine 0.2 g, 0.83 mmol) was added and refluxing continued for a further 6 hours. The mixture was cooled slightly and diluted with ethyl acetate (10 ml) then cooled in ice. The precipitated solid was collected, washed well with ethyl acetate and dried (0.97 g,).

The product was triturated in boiling ethyl acetate for ½ hour and collected from the hot mixture to give the title compound 0.85 g, mp 202°–4° C.

Analysis Found: C, 70.05 H, 5.93, N, 15.59. $C_{26}H_{25}N_5O_2.\frac{1}{4}H_2O$ requires C, 70.33; H, 5.79; N, 15.77;

The maleate ¼H$_2$O salt of the title compound has an m.p. 190°–1° C.

EXAMPLE 3

N-[[[1-(6-Fluoro-2-naphthalenylmethyl)-4-piperidinyl]amino]carbonyl]-6-quinolinecarboxamide N-[[(4-Piperidinyl)amino]carbonyl]-6-quinolinecarboxamide (1.49 g, 5 mmol) was ground in a mortar and pestle and suspended in dry DMF (15 ml) then diisopropylethylamine (0.65 g, 5.04 mmol) was added. To this stirred mixture was added a solution of 2-bromomethyl-6-fluoronaphthalene (1.32 g, 5.02 mmol) in dry DMF (5 ml) over 1 hour. After stirring the mixture for a further 1 hour, more 2-bromomethyl-6-fluoronaphthalene (0.1 g, 0.38 mmol) in dry DMF (2 ml) was added. The mixture was stirred at room temperature overnight then diluted with water (40 ml) to precipitate a solid which was collected, washed well with water and sucked dry on the sinter. This was washed well with diethyl ether, dissolved in chloroform and the solution dried over MgSO$_4$ and evaporated to give a solid (2.38 g).

The product was suspended in boiling ethanol (35 ml) and maleic acid (0.64 g, 5.52 mmol) was added. The mixture was stirred while cooling to room temperature for 3 hours, and the title compound as the maleate salt was collected and dried (1.81 g) mp 200°–1° C. (softens).

Analysis Found: C, 65.02; H, 5.26; N, 9.86; $C_{27}H_{25}FN_4O_2.C_4H_4O_4$ requires C, 65.03; H, 5.10; N, 9.78.

EXAMPLE 4

N-[[[1-(6-Fluoro-2-naphthalenylmethyl)-4-piperidinyl]amino]carbonyl]-6-quinoline carboxamide A solution of 6-isoquinolinoylisocyanate (4.16 g, 5% excess) in CH$_2$Cl$_2$ (20 ml) is added dropwise to a stirred solution of 4-amino-1-[(6-fluoro-2-naphthalenyl)methyl]piperidine (5.2 g, 20 mmol) in CH$_2$Cl$_2$ (100 ml) protected from atmospheric moisture. After addition is completed the reaction is stirred for a further 1 hour, then evaporated. The residue is crystallised from ethanol to give the title compound. m.p. 200°–1° C. (softens maleate salt).

EXAMPLE 5

N-[[[1-(6-Fluoro-2-naphthalenylmethyl)-4-piperidinyl]amino]carbonyl]-6-quinoline carboxamide A mixture of 6-quinolinoyl chloride (4.77 g, 22 mmol), N-[[(6-fluoro-2-naphthalenyl)methyl]-4-piperidinyl]urea (6.02 g, 20 mmol), dry pyridine (2.5 ml) and 1,2-dichloroethane (30 ml) is stirred at reflux for 18 hours. The solution is then cooled, washed with aqueous sodium carbonate solution, dried and evaporated. The residue is crystallised from ethanol to give the title compound, mp 200°–201° C. (softens, maleate salt).

EXAMPLE 6

N-[[[1-(6-Fluoro-2-naphthalenylmethyl)-4-piperidinyl]amino]carbonyl]-6-quinoline carboxamide 2-Bromomethyl-6-fluoronaphthalene (12 g, 50 mmol) is added in one portion to a solution of N-[[[4-pyridyl]amino]carbonyl]-6-quinolinecarboxamide (14.9 g, 50 mmol) in dimethylformamide (50 mol). The mixture is stitted for 2 hours and then diluted with water (100 ml) to precipitate N[[[1-[(6-fluoro-2-naphthalenyl)methyl]-4-pyridinium]amino]carbonyl]-6-quinolinecarboxamide bromide.

The above product is suspended in isopropanol (100 ml), sodium borohydride (6 g, 180 mmol) is added and the mixture stirred at reflux for 16 hours. The solvent is evaporated and the residue triturated with water. The precipitated product is collected and crystallised from ethanol to give the title compound, m.p. 200°–201° C. (softens, maleate salt).

The compounds of the invention are particularly indicated for treating depression in mammals, particularly in man. This invention includes a method of treating depression in a mammal in need thereof, including man, which comprises administering to such mammal an amount effective to alleviate depression of a compound of the formula

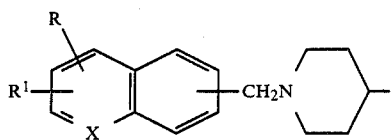

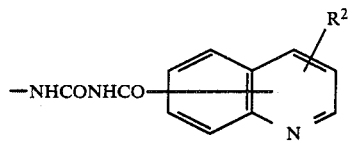

or a physiologically, non-toxic salt thereof. The preferred compounds described above for the compound aspect of the invention are also preferred for this aspect of the invention. The compounds may be administered orally or parenterally.

We claim:

1. A compound of formula

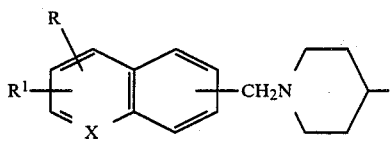

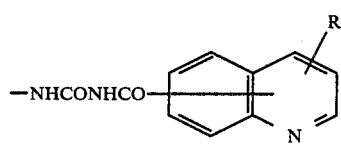

or a salt thereof,
wherein =X— is =CH— or =N—; R and $R^1$, independently, represent hydrogen, halogen or alkoxy of 1 to 6 carbon atoms, and $R^2$ is hydrogen or a substituent selected from halogen, alkyl of 1 to 6 carbon atoms, alkoxy of 1 to 6 carbon atoms, or haloalkyl of 1 to 6 carbon atoms and 1 to 6 halogen atoms.

2. A compound of claim 1 in which one of R and $R^1$ is hydrogen and the other is hydrogen, fluorine, chlorine or methoxy.

3. A compound of claim 1 in which $R^2$ is hydrogen, fluorine, chlorine, trifluoromethyl, methyl or methoxy.

4. A compound of claim 1 in which =X— is =CH— and this moiety, which is bonded to the piperidine ring is a naphth-2-ylmethyl or 6-fluoro-naphth-2-ylmethyl group.

5. A compound of claim 1 in which =X— is =N— and this moiety, which is bonded to the piperidine ring, is quinol-6 or 7-ylmethyl group.

6. A compound of claim 1 wherein the group bonded to the urea function is quinol-6-oyl or quinol-7-oyl.

7. A compound as claimed in claim 1 which is N-[[[1-(2-naphthalenylmethyl)-4-piperidinyl]amino]-carbonyl]-6-quinolinecarboxamide or a pharmaceutically acceptable salt thereof.

8. A compound as claimed in claim 1 which is N-[[[1-(quinol-6-ylmethyl)-4-piperidinyl]amino]-carbonyl]-6-quinolinecarboxamide or a pharmaceutically acceptable salt thereof.

9. A compound as claimed in claim 1 which is N[[[1-(6-fluoro-2-naphthalenylmethyl)-4-piperidinyl]amino]-carbonyl-6-quinolinecarboxamide or a pharmaceutically acceptable salt thereof.

10. A method of treating depression in a mammal in need thereof which comprises administering to such mammal an amount effective to alleviate depression of a compound of formula

wherein =X— is =CH— or =N—, R and $R^1$, independently, represent hydrogen, halogen or alkoxy of 1 to 6 carbon atoms, and $R^2$ is hydrogen or a substituent selected from halogen, alkyl of 1 to 6 carbon atoms, alkoxy of 1 to 6 carbon atoms, or haloalkyl of 1 to 6 carbon atoms and 1 to 6 halogen atoms, or a physiologically, non-toxic salt thereof.

* * * * *